(12) United States Patent
Hurst (10) Patent No.: US 8,894,696 B2
(45) Date of Patent: *Nov. 25, 2014

(54) SUPRACHIASMATIC NUCLEUS INDUCING, MELATONIN SUPPRESSING LIGHT EMITTING DEVICE TO ENHANCE WAKE CYCLE

(71) Applicant: Katherine L Hurst, Coralville, IA (US)

(72) Inventor: Katherine L Hurst, Coralville, IA (US)

(*) Notice: Subject to any disclaimer, the term of this patent is extended or adjusted under 35 U.S.C. 154(b) by 74 days.

This patent is subject to a terminal disclaimer.

(21) Appl. No.: 13/663,428

(22) Filed: Oct. 29, 2012

(65) Prior Publication Data

US 2013/0119886 A1 May 16, 2013

Related U.S. Application Data

(63) Continuation-in-part of application No. 11/623,629, filed on Jan. 16, 2007, now Pat. No. 8,303,635.

(51) Int. Cl.
*A61N 5/06* (2006.01)
*H05B 37/02* (2006.01)
*A61M 21/00* (2006.01)
*G04G 11/00* (2006.01)

(52) U.S. Cl.
CPC ........ *H05B 37/02* (2013.01); *A61M 2021/0044* (2013.01); *A61M 21/00* (2013.01); *G04G 11/00* (2013.01); *A61N 2005/0648* (2013.01); *A61M 2021/0083* (2013.01); *A61N 2005/0642* (2013.01); *A61N 2005/0652* (2013.01)
USPC .................. 607/88; 607/90; 607/91; 607/92; 607/95

(58) Field of Classification Search
USPC ...................................... 607/88–94
See application file for complete search history.

(56) References Cited

U.S. PATENT DOCUMENTS 5,545,192 A * 8/1996 Czeisler et al. ................ 607/88
6,443,977 B1 * 9/2002 Jaillet ............................ 607/88
2005/0248962 A1 * 11/2005 Searfoss, III ................. 362/642

* cited by examiner

*Primary Examiner* — William Thomson
*Assistant Examiner* — William Cheng
(74) *Attorney, Agent, or Firm* — Kirk Hahn (57) ABSTRACT

A light emitting device to awaken or alert an animal by stimulating the Suprachiasmatic Nucleus in the brain to suppress melatonin secretion and change gene expression in the brain. The device can be programmed for an initiation time, color of light, brightness, frequency of pulsating light, and level of gradual intensity. It has the advantage of being silent, does not to disturb other people sleeping in the same room and user is more cognitively alert.

18 Claims, 9 Drawing Sheets

| Light | Disclosed light | Jaillet | Searfoss |
|---|---|---|---|
| Wavelength (nm) | 400 – 700 | White [390 - 750] | White [390 – 750] |
| Intensity (Lux) | 0 – 4,000 | [2,500 – 10,000] alleged | Not disclosed |
| Pulse rate (pulses/hour) | 2 – 36,000 | 144,000 | 0 |

FIGURE 10

SUPRACHIASMATIC NUCLEUS INDUCING, MELATONIN SUPPRESSING LIGHT EMITTING DEVICE TO ENHANCE WAKE CYCLE

RELATED APPLICATIONS

This application is a Continuation-in-Part of U.S. Non-provisional application Ser. No. 11/623,629 filed on Jan. 16, 2007 (pending), the contents of which is herein incorporated by this reference in its entirety. All publications, patents, patent applications, databases and other references cited in this application, all related applications referenced herein, and all references cited therein, are incorporated by reference in their entirety as if restated here in full and as if each individual publication, patent, patent application, database or other reference were specifically and individually indicated to be incorporated by reference.

BACKGROUND OF THE INVENTION

People have been waking up virtually the same way for over 125 years. A desired time to wake up is set and then a loud, irritating often-repetitive, sound is used to awaken the person. Seth Thomas Clock Company was granted a patent in 1876 for a small bedside alarm clock. Technology has made this system a bit easier but the stimulus to wake up remains highly unchanged since the patent was first granted. In 1876, the alarm clock was a fabulous way to indicate when to rise from sleep since sound was easy to produce and it worked. However, a great amount of work on the brain and how sensory information is processed has been conducted since 1876.

Although sound was an excellent way to wake someone up in 1876, studies of the brain and sensory system has shown sound has absolutely nothing to do with the regulation of sleep and wake cycles, and therefore the use of sound to awaken somebody from sleep is an antiquated method for the $21^{st}$ century.

The brain has been designed to quickly receive and process information relayed by sound due to its importance in the survival of the species. The auditory cortex in the human brain is the special area used to process sound. The auditory cortex allows communication between and among humans. Language is processed there and speech is also initiated there. The auditory cortex has nothing to do with sleep wake cycles.

Figure 1:
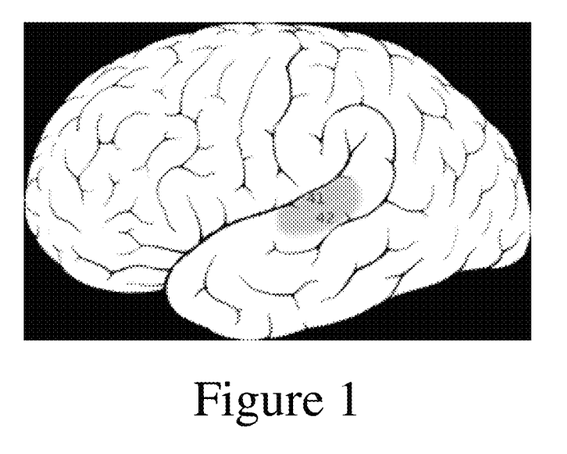

Studies of the wake/sleep cycle have demonstrated an interesting and wonderful system for its regulation—light. The light is sensed by the eyes and travels on the second cranial nerve (optic nerve) to a nucleus in the brain called the suprachiasmatic nucleus (FIG. 1). When light intensity is low, the suprachiasmatic nucleus signals the pineal gland to produce a hormone called melatonin, which causes the feeling of drowsiness. There is also a set of proteins, RNA, other cell chemicals made by cells in the suprachiasmatic nucleus that either turn on or off production of products with regard to light stimulus. When light intensities are high, the production of melatonin is inhibited.

The suprachiasmatic nucleus system is so sophisticated that even people who are blind still respond to changes in light intensity through melatonin level fluctuations. This supports a separate tract for the sensory input and response to light stimulus for regulating the sleep/wake cycle.

Human physiology and behavior is dominated by near-24-hour rhythms that have a major impact on our health and well-being. For example, alertness and performance patterns, core body temperature rhythms and the production of hormones, such as, melatonin and cortisol are all regulated by an endogenous near-24-hour oscillator in the suprachiasmatic nuclei (SCN) of the anterior hypothalamus. Light information is captured by specialized retinal photoreceptors and sent directly to the SCN along a dedicated neural pathway, the retinohypothalamic tract (RHT). The intensity, number, duration, pattern and timing of exposure to light, as well as, the wavelength of light have been shown to regulate to circadian resetting. The human brain is extremely sensitive to dim light. A light intensity equivalent to indoor room light is able to significantly effect changes in hormone release. The wavelength of the light is important in humans with an increased sensitivity to short wavelength light and spectral sensitivity which is different from conventional scotopic and photopic vision.

It is inevitable, even though light is the correct stimulus to awaken a person, for a desensitization to occur over time. Adaption to a stimulus eventually occurs so it must be changed in order to be effective. If a person sets a device at a frequency, color and/or intensity, it may wake them up very well for a while, but in a few months or years, they may sleep right through the light stimulus. Alarms clocks can be loud and annoying but people sleep right through them because their brain has adapted to the stimulus.

Additionally, a light stimulus does what sound cannot, decrease melatonin and change the gene expression of the cells in the SCN. Melatonin and the cell expression cause lethargy, decreased alertness, cognitive decline and sleepiness. People hate early morning because they feel sleepy and tired. They feel this way because they woke up with a system that does not depress the levels of melatonin or change the cell signaling in the SCN.

The pineal gland synthesizes and secretes melatonin, a hormone that communicates information about environmental lighting to various parts of the body. Melatonin has the ability to entrain biological rhythms and has important effects on reproductive function of many animals.

Figure 2:
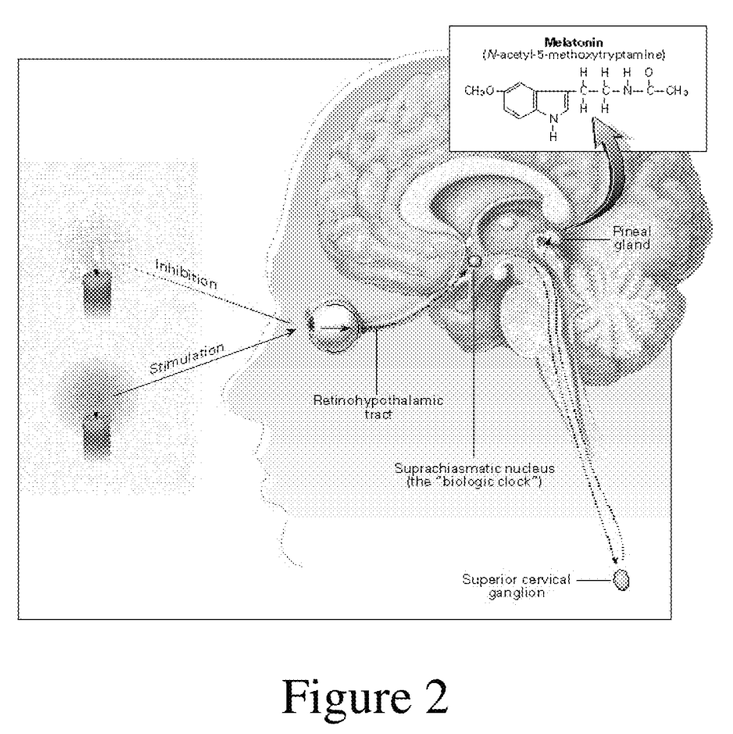
Figure 3:
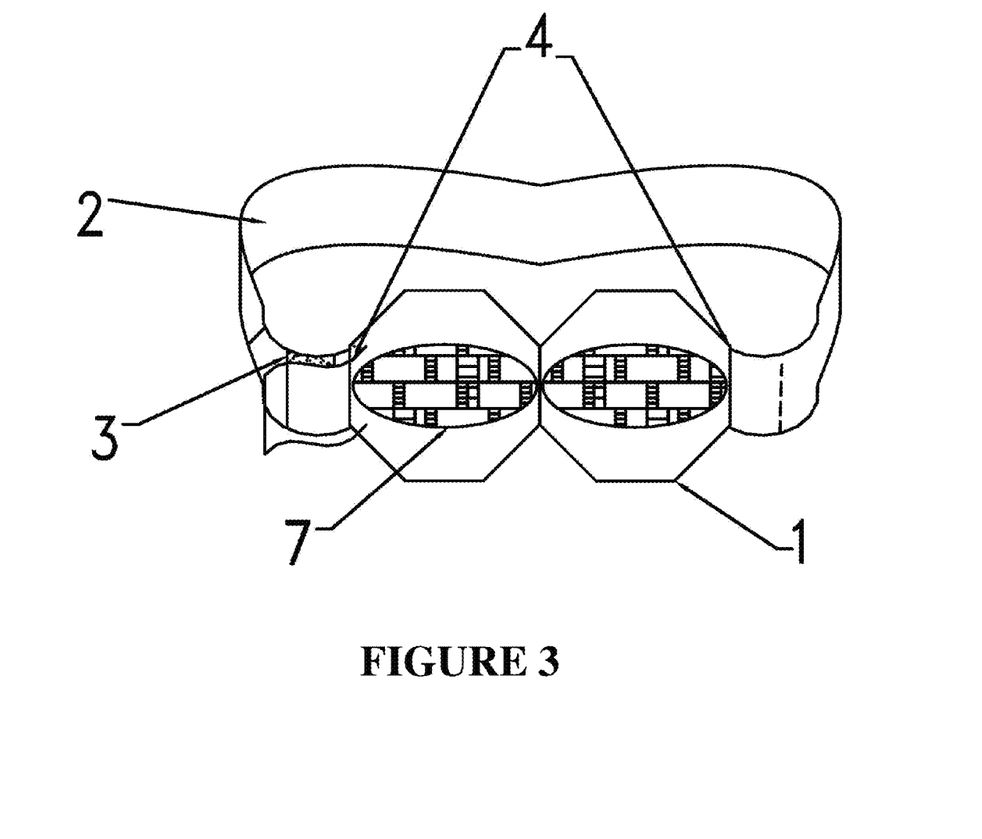
Figure 4:
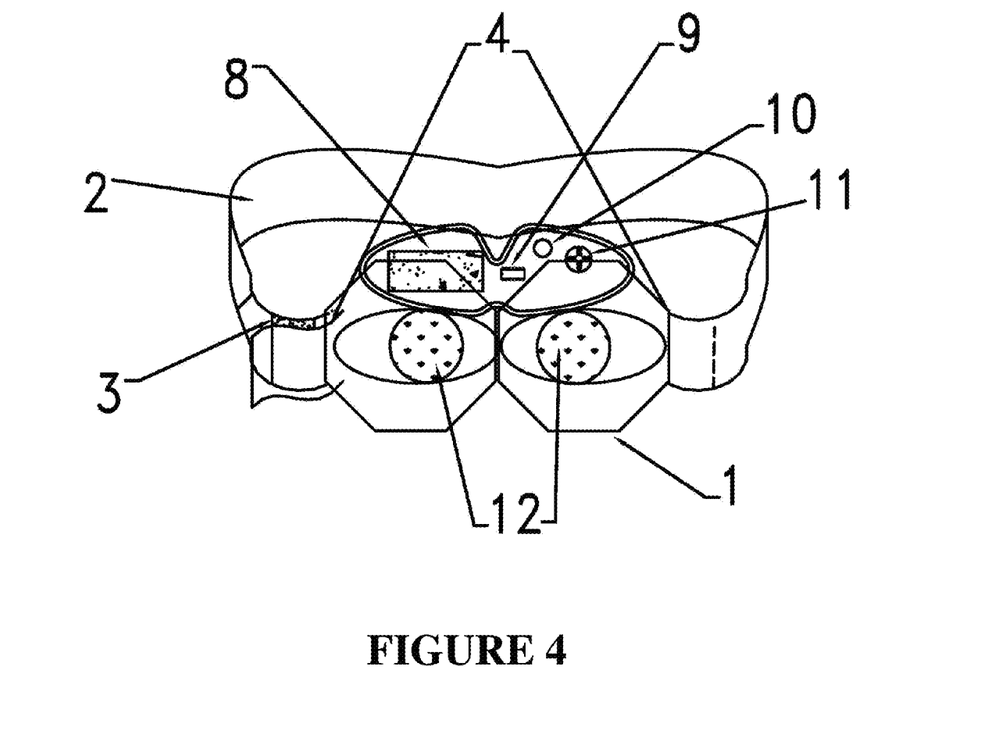
Figure 5:
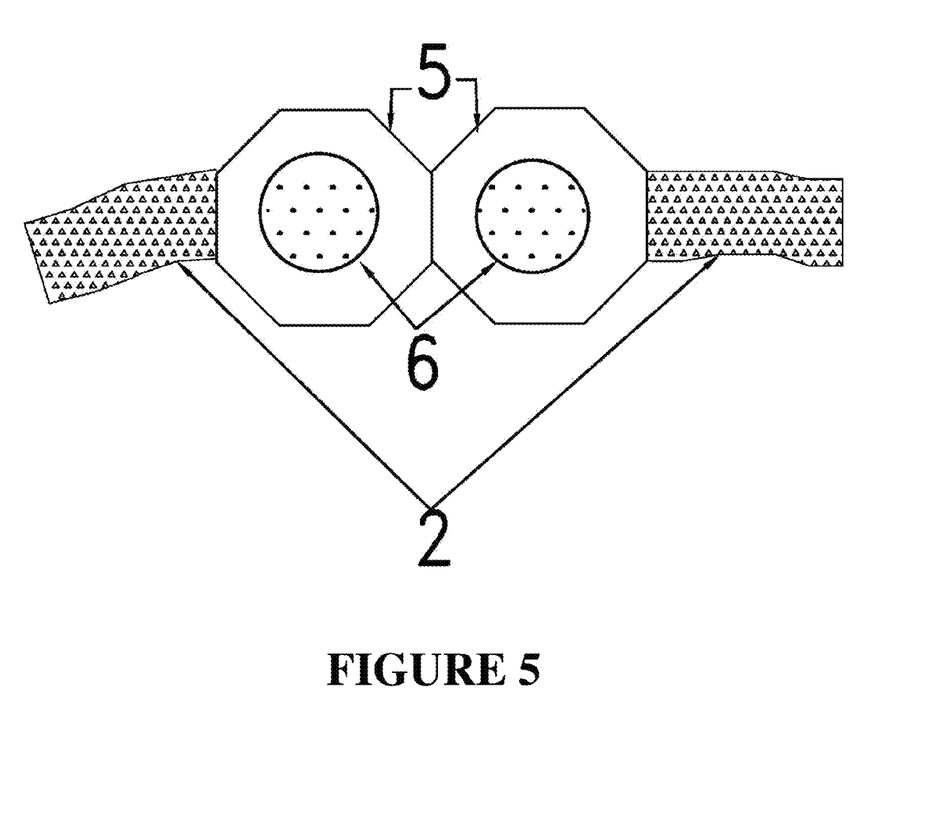
Figure 6:
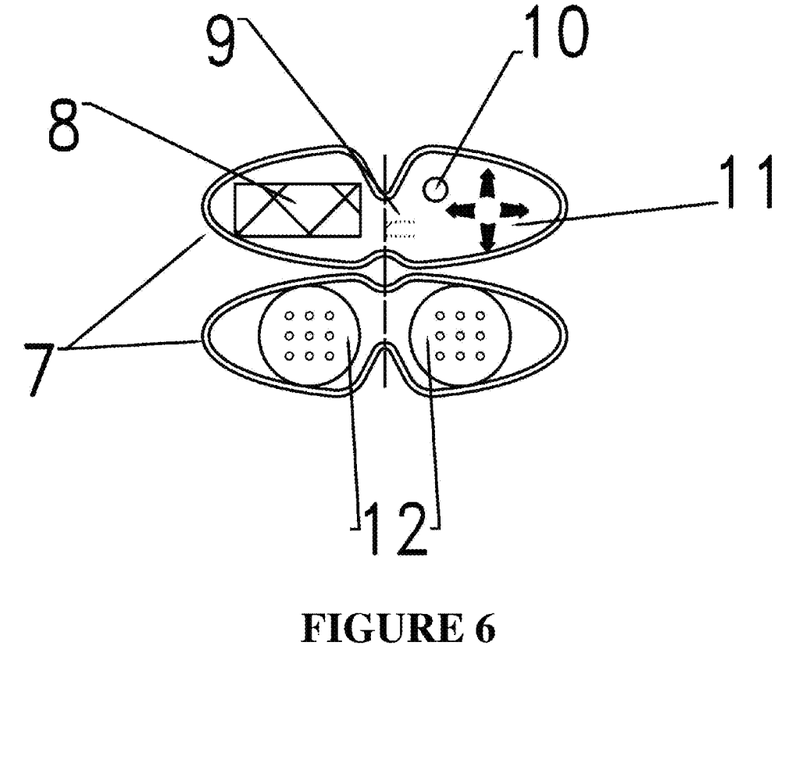
Figure 7:
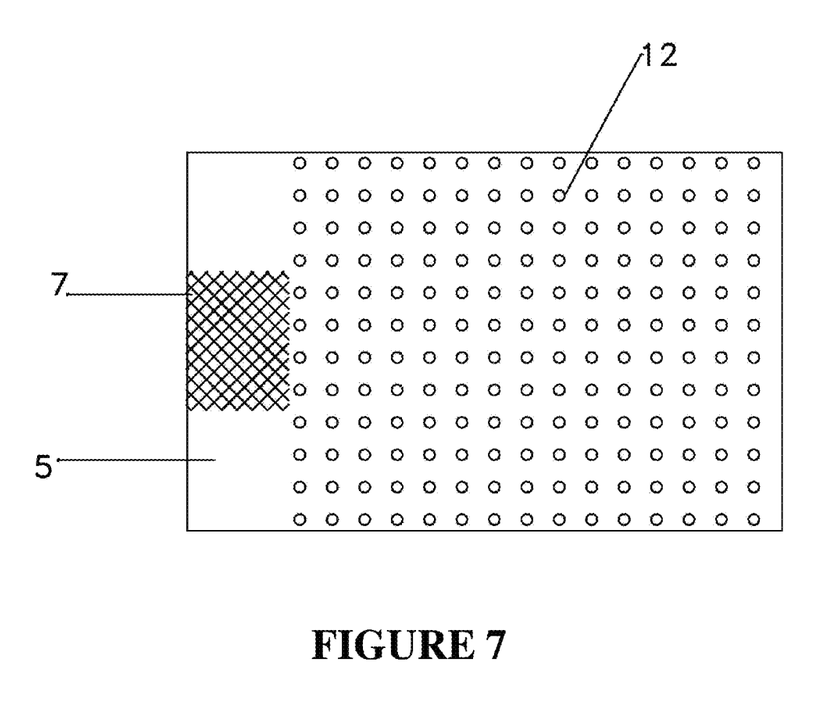
Figure 8:
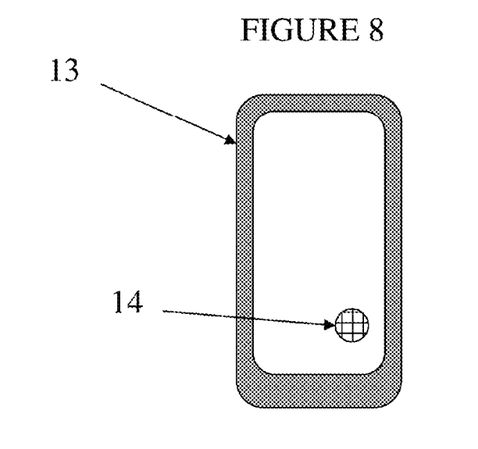
Figure 9:
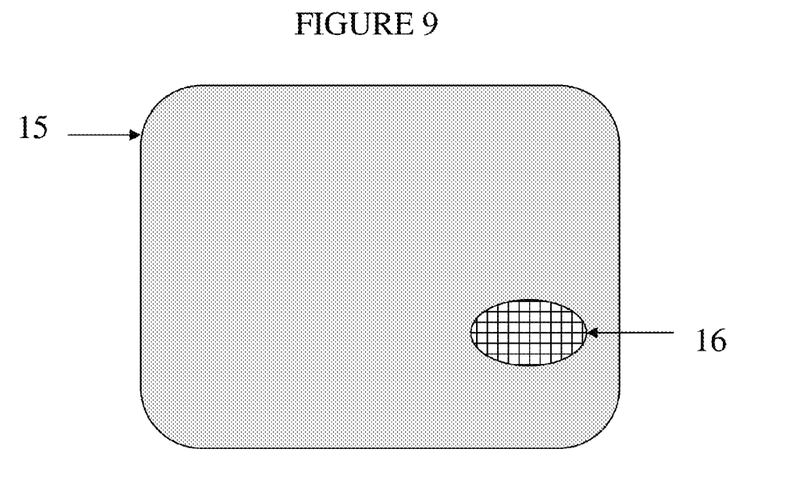

The pineal gland is a small organ shaped like a pine cone. The pineal gland is composed of "pinealocytes" and glial cells. It is located on the midline, attached to the posterior end of the roof of the third ventricle in the brain (FIG. 2).

The precursor to melatonin is serotonin, a neurotransmitter that itself is derived from the amino acid tryptophan. Synthesis and secretion of melatonin is dramatically affected by light exposure to the eyes. The fundamental pattern observed is that serum concentrations of melatonin are low during the daylight hours, and increase to a peak during the dark. The circadian rhythm in melatonin secretion in humans is that blood levels of melatonin are essentially undetectable during daytime, but rise sharply during the dark. Other species have very similar patterns. The duration of melatonin secretion each day is directly proportional to the length of the night.

Melatonin has important effects in integrating photoperiod and affecting circadian rhythms. Consequently, it has been reported to have significant effects on reproduction, sleep-wake cycles and other phenomena showing circadian rhythm.

Seasonal changes in day length have profound effects on reproduction in many species, and melatonin is a key player in controlling such events. In temperate climates, animals like hamsters, horses and sheep have distinct breeding season. During the non-breeding season, the gonads become inactive (e.g., males fail to produce sperm in any number), but as the breeding season approaches, the gonads must be rejuvenated. Photoperiod—the length of day vs. night—is the most important cue allowing animals to determine which season it is. The pineal gland is able to measure day length and adjust secretion of melatonin accordingly.

The effect of melatonin on reproductive systems can be summarized by saying that it is anti-gonadotropic. In other words, melatonin inhibits the secretion of the gonadotropic hormones luteinizing hormone and follicle-stimulating hormone from the anterior pituitary. Much of this inhibitory effect seems due to inhibition of gonadotropin-releasing hormone from the hypothalamus, which is necessary for secretion of the anterior pituitary hormones. One practical application of melatonin's role in controlling seasonal reproduction is found in its use to artificially manipulate cycles in seasonal breeders.

The disclosed light emitting device is different from other devices that appear similar, although only superficially. There are products that use a face covering to block out light and may play music or other sounds to sooth the person into sleep or induce a perceived good sleep experience. Although these devices may appear similar, they are meant to function in the opposite of the disclosed light emitting device in that they are trying to make a person sleep better, while the disclosed device is meant to awaken a person from sleep.

There are some devices that have a face covering and emit light from the face covering to modify the circadian rhythm in a person. These devices, although emitting light, are not worn when sleeping or used to awaken a person like an alarm clock but instead are meant to combat jet lag or fatigue, or to increase beta-endorphins in the bloodstream of the subject.

There are devices that appear "on the surface" to be similar to the disclosed devices in the application; however, they fail to have the combination of wave length, duration, initiation of onset, termination of duration, pulse rate, and intensity that is used to awaken a sleeping animal, including humans.

There are devices that use pulsing light to put people to sleep [Kameyama US20070118026; Searfoss et al. US 20050248962], alleviate "jet lag", re-set a person's circadian rhythm (biorhythm) [Czeisler U.S. Pat. No. 5,304,212], or treat a medical condition [Jaillet U.S. Pat. No. 6,443,977; Molina US20050070977; Brainard US20010056293]. However, there has never been a device that uses the claimed combination of wave length, duration, initiation of onset, termination of duration, pulse rate, and intensity to awaken a sleeping animal, including humans. It is impossible to extrapolate from devices and methods used to put a person to sleep or change their circadian rhythm to devices and methods used to awaken a person. It is a simple fact that something that puts a person to sleep does not at the same time awaken a person.

The disclosure of a device or method that functions to induce a specific phenomenon in a person does not anticipate or make obvious a device or method that induces the opposite phenomenon in a person. That is, a device or method that induces sleep in a person does not anticipate or make obvious a device or method that induces awakening in a person.

Kameyama US20070118026 discloses a device to put an awakened person back to sleep or to put an awake person to sleep by "a lighting device to irradiate a light in a waveband with relatively small melatonin-production suppression effect" (Abstract).

Searfoss et al. US 20050248962 discloses a person exposed to "cycling the light at a frequency of one cycle per second to one cycle per minute" will go to sleep. Searfoss discloses the use a full spectrum light with no pulses for a "wake-up mode"

Czeisler U.S. Pat. No. 5,304,212 discloses a method to re-set a person's circadian rhythm after travel to a distant time zone where the natural photoperiod is different from the person's previous circadian rhythm. The disclosed method involves exposing a conscious person to a pulse of light to delay the onset of a person's natural sleep phase or induce sleep in a person. Czeisler discloses the use a single light pulse at a high intensity to re-set a person's circadian rhythm. He discovered that bright light is necessary to rapidly achieve phase modification. When bright light, on the order of 7,000-12,000 lux (optimally averaging about 9,500 lux or greater in the preferred embodiment) is applied daily, phase shifts on the order of 9-11 hours in a 2-3 day period are commonly observed. Czeisler '212 method uses a single pulse of light with a high intensity and adapted to delay the onset of a person's sleep phase; which is the opposite of the function of the disclosed device in the application.

Jaillet U.S. Pat. No. 6,443,977 discloses a pulse rate of 25 Hertz (25 pulses/second) or a pulse rate of 2,400 pulses/minute and the apparatus is applied to a conscious person. The apparatus and method in Jaillet '977 is used for reconfiguring or redirecting nervous impulses to treat the symptoms of dyslexia, Attention Deficit Disorder (ADD) and Attention Deficit Hyperactive Disorder (ADHD).

Molina US20050070977 discloses a device to alleviate assorted ailments (diabetic skin ulcers, severe oral sores cause by chemotherapy and radiation, premenstrual syndrome, headaches, seasonal affect disorder, labor, jet lag, sleep disorders and eating disorder). The device is used on a conscious person with a pulse rate up to 70,000 pulses/minute.

Brainard US20010056293 discloses a device adapted to treat "mammals with a wide variety of disorders or deficits, including light responsive disorders, eating disorders, menstrual cycle disorders, non-specific alerting and performance deficits, hormone-sensitive cancers, and cardiovascular disorders". Additionally, Brainard does not disclose any pulse rate and the device is used on a conscious person.

None of these devices use the combination of wave length, duration, initiation of onset, termination of duration, pulse rate, and intensity to awaken a sleeping animal, including humans.

The disclosed light emitting device takes advantage of the modern discoveries in medicine and brain physiology. The device allows a subject to awaken from sleep at a predetermined time, while achieving a reduction in drowsiness.

BRIEF SUMMARY OF THE INVENTION

The light emitting device is meant to replace the conventional alarm clock. Sound is not used at all, this alarm is silent. A person can program the mask with a desired wake up time, color of light, brightness, frequency of pulsating light, and level of gradual intensity. It has been shown that a pulsating light is the best stimulus to depress melatonin levels in humans. A preferred method is a pulsating light of a wavelengths 450-460 nm. The importance of a pulsating light has only recently been discovered as a factor in melatonin production. The disclosed device is able to depress melatonin slowly over time to a comfortable level to make early mornings become productive and pleasant.

The disclosed device combines physiology, neuroscience, endocrinology, evolutionary biology, engineering, and research to produce a new and improved alarm system.

The user can adjust the awakening sequence (initiation, duration, pulse rate, wave length, intensity, etc,) to obtain a routine that best suits them.

The disclosed device can be used by anybody to avoid oversleeping. Mornings are more productive when a person does not feel drowsy or tired. Additionally, it has the added advantage of being silent so as not to disturb other people sleeping in the same room as usually caused by loud alarm clock. A spouse or roommate can comfortably sleep beside a person who has to wake up at 5:00 AM without being bothered. The disclosed device can have a lens that plane polarizes the light and cuts out UV light for comfort and safety. The disclosed device is safe to use during sleep since no wires or external output are needed when used as a face covering.

The disclosed device can use any source for the producing the correct light wavelengths and pulses. The use of an LED as the light source has several advantages. An LED is a low energy, high output device and reduces the need for replacing burned out units. An LED light source can produce light of varying intensity, wavelength and pulsate rate. The energy needs are very low so it can be powered by batteries and still function for long periods. A small computer can be included with the disclosed device so no external input is required. A menu or display allows a person to personalize their wake up alarm. The system can have memory so a person can save an awake routine. The disclosed device, in one design, can be a mask worn while a person is sleeping and easily removed in the morning. The mask is soft and fits over the eyes. The computer unit can be imbedded into the mask and programmed to send the wake up signal or shut off.

The mask can have a foam case that is lightweight and comfortable. The light source or LED can be embedded deep in the foam so the person does not feel them. However, the foam allows the light source or LED to create a bright light to stimulate properly the user.

The controls (control center) and power source can be included in the mask and covered with soft material. After being programmed, they can be hidden to allow the user to sleep comfortable. A well-fitted mask would be the best way to deliver the light but other alternates are possible as well.

The disclosed device can have other designs using the same principles of preprogrammed pulsating light—a pillow or pillow case, a device next to the bed (e.g., table, bed post, head board, etc.), a device hanging on the wall, a personal digital assistant, a smart phone, a smart tablet, a smart device or a device located in any place used for sleeping so the light enters the eye.

A general definition of a smart phone is a device that combines a cell phone, also called a mobile phone, with a hand-held computer, typically offering Internet access, data storage, e-mail capability, etc.

A general definition of a smart device is a device that may or may not have a phone, that is digital, active, computer networked, is user reconfigurable and that can operate to some extent autonomously.

A smart device is an electronic device that is cordless (unless while being charged), mobile (easily transportable) that combines two or more features of being able to connect to the internet by WiFi or phone data service, capable of voice communication, capable of video communication, internet browsing, mapping or operate to some extent autonomously.

A non-exclusive list of some examples is Apple iPhone, Apple iPad, Blackberry, Samsung Galaxy tablet.

The programs that run on smart devices are called "apps", which is short for applications. Apps also are software programs.

An app is defined as a piece of software; which can run on the Internet, a computer, a smart device, a smart phone, a tablet or other electronic device. A general definition of an app is "an application utilizing web and browser technologies to accomplish one or more tasks over a network, typically through a browser" or "computer software designed to help the user to perform singular or multiple related specific tasks".

Currently there are 3 major operating systems for apps—Apple iOS, Google Android and Microsoft Windows. There are many different technologies that are used to create web apps—Flash, JavaScript, HTML5, CSS, PHP, Java, Silverlight—to just mention a few.

Apps can be used with the internet or intranet. Common browsers are Firefox, Chrome, Safari, Opera, and Internet Explorer.

An important feature of the disclosed device is the light intensity used in combination with the pulse rate and frequency of light (i.e., color of light). Light intensity is measured in "lux". Light intensity [lux] must not be confused with light illumination [lumens], since they are two different features of light and "lux" cannot be converted to "lumens" and vice a versa.

Lux (symbol: lx) is the SI unit of light intensity measuring luminous power per area $[lm/m^2]$.

Lumen (symbol: lm) is the SI derived unit of luminous flux measuring the total "amount" of visible light emitted by a source.

As can be seen by the units for Lux $(lm/m^2)$ and Lumen (lm), they are not equivalent nor can they be converted from one to the other.

Any given Lux value can have an infinite number of Lumen values [lux: $x=lm/y^2$; where y=any positive number; therefore lumen: $lm=xy^2$, where $xy^2$=any positive number].

And the converse is also true; any given Lumen value can have an infinite number of Lux values [lumen: $x=lx \cdot y^2$; where y=any positive number; therefore lux: $lx=x/y^2$, where $x/y^2$=any number≥0 (note: the value of any number divided by ∞ is zero].

The relationship between Lux and Lumens is analogous to the relationship between Force (N—Newtons) and Pressure $(N/m^2$—Pascals) or Distance (miles) and Acceleration $(miles/sec^2)$.

A person skilled in the art knows that all qualities of light (intensity, wavelength, duration of exposure) are of importance to the light's effect on an animal.

For example, in a study of light sensitivity of Atlantic salmon, European sea bass and Atlantic cod, the effect of different intensities and narrow bandwidth lights on nocturnal melatonin suppression showed a clear species specific light intensity and spectral sensitivities, with cod being from 100 to 1000 times more sensitive than sea bass and salmon [Vera et al., 2010, Differential light intensity and spectral sensitivities of Atlantic salmon, European sea bass and Atlantic cod pineal glands ex vivo, Gen Comp Endocrinol., 165(1):25-33].

In a study of mice, different strains were exposed to different intensities of white fluorescent light (100, 0.14, 0.017 lux in both strains and 0.0021 and 0.00026 lux in CBA mice). In C3H mice, the threshold of light intensity to suppress pineal melatonin content was between 0.14 and 0.017 lux, whereas that in CBA mice was between 0.0021 and 0.00026 lux." [Goto et al., 1990, The influence of different light intensities on pineal melatonin content in the retinal degenerate C3H mouse and the normal CBA mouse, Neuroscience Letters, 108(3), 267-272].

Figure 10:
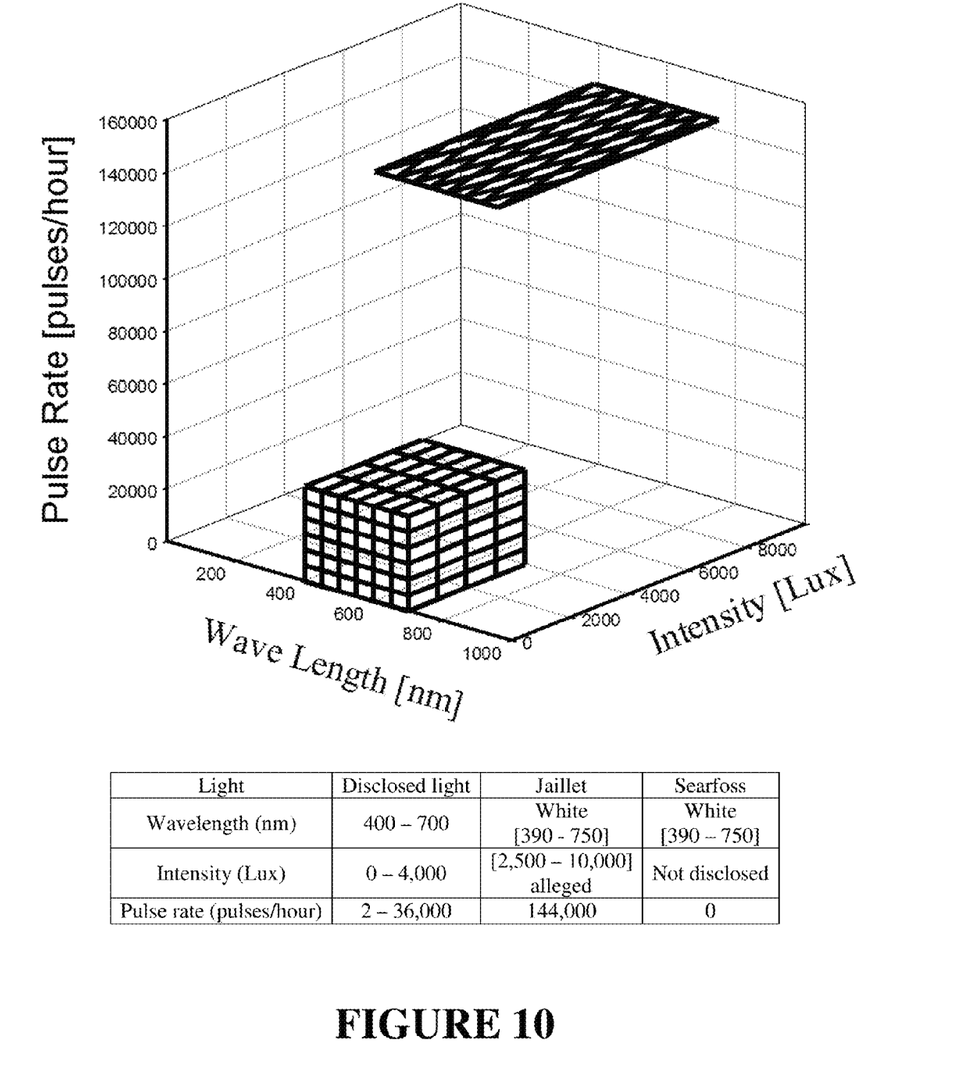

In a study with mice infected with the Venezuelan equine encephalomyelitis (VEE) virus, the serum levels of melatonin remained constantly elevated when they were exposed to 2500 lux with a 12 hour light: 12 hour dark photoperiod. In mice exposed to 400 lux, low levels of serum melatonin were detected during the day and high levels during the night. An increase in the survival rate of the infected mice from 6 to 13 days after virus inoculation was also observed. The significant increment in the concentration of serum melatonin produced by the high intensity light could be responsible for the longer survival rate of mice infected with the VEE virus." [Medina et al., 2001, Exposure to 2500 Lux Increases Serum Melatonin in Venezuelan Equine Encephalomyelitis, Neurochemical Research, 24(6), 775-778]

Therefore, it is incorrect to think of the parameters of "light" [wave length, duration, initiation of onset, termination of duration, pulse rate, and intensity] as being separate and distinct entities that can be viewed individually without considering the other parameters present at the same time. All the parameters of the "light" must be considered together when evaluating the effect produced by that light.

For example, if a device emits a light of X frequency with a Y pulse rate and produces effect Z and another device emits a light of U frequency with a V pulse rate and produces effect W, it is impossible to know or predict what effect will be produced by a device that emits a light of X frequency with a V pulse rate or emits a light of U frequency with a Y pulse rate.

BRIEF DESCRIPTION OF THE SEVERAL VIEWS OF THE DRAWING

FIG. 1 illustrates the area [auditory cortex] in the human brain used to process the sense of sound.

FIG. 2 illustrates the suprachiasmatic nucleus in the human brain and physiology of melatonin secretion (Brzezinski A., N Engl J Med, 1997, 336:186-195).

FIG. 3 illustrates the light emitting device as a face mask.

FIG. 4 illustrates the light emitting device as a face mask with the case containing the controls (control center) and display open during use.

FIG. 5 illustrates the inner surface (surface contacting the face) face mask version of the light emitting device.

FIG. 6 illustrates the case containing the controls (control center) and display.

FIG. 7 illustrates a pillow containing the controls (control center) and display.

FIG. 8 illustrates a smart phone containing a display with an icon for the program using light to awaken a mammal or signal a timing event with light.

FIG. 9 illustrates a smart tablet containing a display with an icon for the program using light to awaken a mammal or signal a timing event with light.

FIG. 10 illustrates a 3D graph showing the combination of the parameters of light. The X-axis is wavelength (nm); the Y-axis is intensity (lux) and Z-avis is pulse rate (×1,000 pulses/hour).

DETAILED DESCRIPTION OF THE INVENTION

The disclosed device uses pulses of light directed at the eyes of a subject to awaken them from sleep. Although the device can be in any design or format that accomplishes the needed impulses to simulate a subject from sleep, a mask is a preferred design. The mask has a band to attach the mask to the face of the user. The shape of the mask is designed to house the electronics, fit comfortably, block light from outside and be stylish. Various materials can be used to make the mask. The material should be sturdy, lightweight, durable, and block light. The side of the mask facing the user can have a light weight, soft foam that rests against the user. The foam has holes for the light source, and plane polarizing, UV light blocking lenses, which provides a distance from mask and eyes, and comfort for the user. The mask can be used with or without the control center. The control center can be easily removed from the mask when it needs to be replaced due to wear and tear. A replacement mask will accept the original control center and the original worn out mask can be thrown away.

A LED array made of a variety of colors is arranged and connected to a logic chip. The logic chip is able to program the array to turn on at a set time, and have a specific color, pulsation rate, and intensity. The chip will have memory to save routines. The chip also may provide a random surprise wake up signal with unknown color, intensity and pulsation rate. A battery source, a screen, and connections to all components will be housed in the control center. The case will be made from a light weight material. The control center is able to be separated from the mask. The case can be opened for programming and easily closed after programming.

An alternative to the mask design of the disclosed device is a pillow unit with the previously described components. The foam is large enough the fit inside a typical pillow case and the control center is covered to protect its electronic components. The electronics is housed within the pillow with the LEDs embedded in the pillow. The LEDs are covered with a plane polarizing UV light blocking lens, if needed.

Another alternative design to the disclosed device is a bedside apparatus. It can be attached to a head board on a bed or on a nearby table.

FIG. 3 shows the light emitting device as a face mask with the band 2 connected to the mask 1 by a loop 4 passing through the mask 1. The end of the band is retained by an attachment site 3. Contained within the mask 1 is a case 7.

FIG. 4 shows the light emitting device as a face mask with the case 7 flipped open to show the contents. The case 7 has on the top cover a screen 8, a logic chip 9, a battery 10, and the controls (control center) 11. The mask 1 has the light source arrays 12 underneath the case 7 cover.

FIG. 5 shows the light emitting device as a face mask with the inside (surface touching face) of mask 1. The inside of the mask 1 has a layer of soft material or foam 5. Over the area where the person's eyes would be located are lenses 6.

FIG. 6 shows a close-up of the case 7. The top of the cover has the screen 8, logic chip 9, battery 10, and controls (control center) 11. The bottom of the case 7 has the light source arrays 12.

FIG. 7 shows the light emitting device as a pillow covered with a layer of soft material or foam 5. The pillow has a case 7 containing the controls (control center) that regulates the light source arrays 12 on the outside of the pillow.

FIG. 8 represents a smart phone with icons on the display panel. The tapping the icon selects the claimed program and allows the user to change parameters (light frequency (color), pulse rate, light intensity, time of onset, time duration between renewed activation, etc.) of the light awakening process.

FIG. 9 represents a smart tablet with icons on the display panel. The tapping the icon selects the claimed program and allows the user to change parameters (light frequency (color), pulse rate, light intensity, time of onset, time duration between renewed activation, etc.) of the light awakening process.

The disclosed device and method use the combination of wave length, duration, initiation of onset, termination of duration, pulse rate, and intensity to awaken a sleeping animal, including humans; and it is the specific combination of these features that achieves the disclosed result of awakening a sleeping animal. The combination of features should be viewed as 3-, 4-, 5- or 6-dimensional spaces where each value corresponds to a specific point in space (FIG. 10).

The effect of the light to awaken a subject requires that the disclosed parameters exist at the same time within the boundaries of the effective zone. The light cannot be considered as if it were three separate components in a machine. Each combination of the parameters of light—e.g. wavelength, intensity (lux) and pulse rate—produces a unique response in the brain. This feature is best illustrated by FIG. 10.

A single type of light is represented by a single point in the 3D space of X (wavelength), Y (lux) and Z (pulse rate [×1,000 pulses/hour]). This graph illustrates the disclosures in Jaillet '977 and Searfoss et al. (US 20050248962), and compares them to the claimed light in Claim 1.

The box along the X-axis illustrates a range of light [400-700 nm×0-4,000×2-36,000].

The plane near the top of the Z-axis shows the disclosed values in Jaillet '977 [390-750×2,500-10000×144,000].

The point that would represent the disclosure in Searfoss '962 cannot be shown in this graph because it is too small [390-750×0×0] since Searfoss '962 does not disclose a lux value and the light is constant (0 pulses/hour).

An examination of the graph shows there is no overlap between the disclosed light and a light from a combination of Jaillet '977 and Searfoss '962. There is no overlap between the disclosed light and this combination. The true test of evaluating different light sources with different parameters is to find a light source that has some of the disclosed parameters at the same time (i.e., there would be overlap in a 3D graph).

For example, a light intensity disclosed for the treatment of Seasonal Affective Disorders (SADS) would not suggest to a person skilled in the art that this treatment could be used to awaken a sleeping subject. There is no known correlation that would suggest to a doctor or a person working in sleep research to use a method to awaken a sleeping person that was developed for the treatment of a person with SADS.

Additionally, some of these devices make dubious claims as to their effectiveness for treating neurological symptoms. The device and methods disclosed in Jaillet '977 to "reconfigure or redirect nervous impulses to treat the symptoms of dyslexia, Attention Deficit Disorder (ADD) and Attention Deficit Hyperactive Disorder (ADHD)" do not have strong medical evidence to support that they are an effective treatment for these ailments. These devices or methods lack endorsements by the American Academy of Pediatrics or the American Psychiatric Association. The neural pathways to the parts of the brain involved are not reached by the optic nerve and light is not all correlated with therapeutic gains in these diseases. Even if this device and method worked for these symptoms they would not be appropriate for awakening a person from sleep. There is no correlation between a person with these disorders and a normal healthy person sleeping.

An important aspect of the disclosed devices and methods is that a person is more alert and cognitively functioning faster with the proper light stimuli rather than with a sound alarm. Vandewalle et al. 2011 found when compared to longer wavelength light, shorter wavelength light exposure increases ongoing nonvisual cognitive activity in subcortical and cortical brain areas. Compared with green light, 1 minute of low intensity blue light was able to significantly increase brain activity in a widespread set of higher order cortical areas, including the frontopolar, lateral prefrontal and premotor cortex, intraparietal sulcus, insula, cerebellum, and thalamus, which are all known to be involved in executive control and working memory.

The rate of pulsating the light is important to the disclosed devices and methods since science has proven in humans and animals this stimulation is superior to continuous light stimulation. It has been reported in studies of nocturnal animals that the mammalian circadian system is responsive to brief exposures of light. Nelson and Takahashi 1991 demonstrated that pulses of bright light as short as 3 seconds produced measurable phase shifts in the golden hamster. They also showed that extending the duration of the stimulus beyond 5 minutes produced little additional phase shift.

Gronfier et al. 2004 demonstrates that a single sequence of intermittent bright light pulses can phase delay the human circadian pacemaker and shows that intermittent pulses of light has a greater resetting efficacy on a per minute basis than does continuous exposure to light.

Medical training and experience with patients were used to develop the disclosed methods and devices that use the method. The specific characteristics and qualities of light have a profound effect on the human brain and a human's behavior. Light with the disclosed light parameters produced superior results. Up to the present, no known method or device takes advantage of this knowledge.

Embodiments

In one embodiment the device is a face covering device. In another embodiment the device is a mask. In another embodiment the device is a shield. In another embodiment the device is a free-standing device. In another embodiment the device is a lamp. In another embodiment the device is a pillow case. In another embodiment the device is wall-mounted device. In another embodiment the device is a pair of glasses. In another embodiment the device is a television. In another embodiment the device is a plasma screen. In another embodiment the device is a LCD screen.

In one embodiment the band is elastic. In another embodiment the band is cloth. In another embodiment the band is plastic. In another embodiment the band is a string. In another embodiment the band is rubber. In another embodiment the band is a cord. In another embodiment the band is a flexible material.

In one embodiment the attachment is VELCRO™ (generic: hook and loop fastener). In another embodiment the attachment is adhesive. In another embodiment the attachment is a buckle. In another embodiment the attachment is a sliding clasp. In another embodiment the attachment is a knot. In another embodiment the attachment is a button. In another embodiment the attachment is a snap. In another embodiment the attachment is a hook.

In one embodiment the inner surface of the face covering is foam. In another embodiment the inner surface of the face covering is cloth.

In one embodiment the lenses are glass. In another embodiment the lenses are plastic. In another embodiment the lenses are filters to select the proper wave length of light.

In one embodiment the light source is a light bulb. In another embodiment the light source is a light emitting diode (LED). In another embodiment the light source is a liquid crystal display (LCD). In another embodiment the light source is a plasma display. In another embodiment the light source is a multi-frequency light source with a filter.

In one embodiment the controls are digital. In another embodiment the controls are analog. In another embodiment the controls are toggles. In another embodiment the controls are push buttons.

In one embodiment the timer is electronic. In another embodiment the timer is mechanical. In another embodiment the timer is external from the device. In another embodiment the timer is external from the device.

In one embodiment the initiation of the awakening series of events is by a timer. In another embodiment the initiation of the awakening series of events is by an external electronic signal. In another embodiment the initiation of the awakening series of events is by a pager. In another embodiment the initiation of the awakening series of events is by a phone call.

In another embodiment the initiation of the awakening series of events is by a cell phone call. In another embodiment the initiation of the awakening series of events is by an e-mail.

In one embodiment the light emitting device awakens an animal. In another embodiment the light emitting device awakens a mammal. In another embodiment the light emitting device awakens a pet. In another embodiment the light emitting device awakens dog or cat. In another embodiment the light emitting device awakens domestic animals. In another embodiment the light emitting device awakens a commercial production of animal. In another embodiment the light emitting device awakens a pig, cow, or chicken. In another embodiment light emitting device awakens a primate. In another embodiment light emitting device awakens a human.

In one embodiment the light emitting device stimulates hormone production in an animal. In another embodiment the light emitting device stimulates hormone production in a mammal. In another embodiment the light emitting device stimulates hormone production in a pet. In another embodiment the light emitting device stimulates hormone production in dog or cat. In another embodiment the light emitting device stimulates hormone production in domestic animals. In another embodiment the light emitting device stimulates hormone production in a commercial production of animal. In another embodiment the light emitting device stimulates hormone production in a pig, cow, or chicken. In another embodiment light emitting device stimulates hormone production in a primate. In another embodiment light emitting device stimulates hormone production in a human.

In one embodiment the light emitting device inhibits hormone production in an animal. In another embodiment the light emitting device inhibits hormone production in a mammal. In another embodiment the light emitting device inhibits hormone production in a pet. In another embodiment the light emitting device inhibits hormone production in dog or cat. In another embodiment the light emitting device inhibits hormone production in domestic animals. In another embodiment the light emitting device inhibits hormone production in a commercial production of animal. In another embodiment the light emitting device inhibits hormone production in a pig, cow, or chicken. In another embodiment light emitting device inhibits hormone production in a primate. In another embodiment light emitting device inhibits hormone production in a human.

In one embodiment the light emitting device has a power source. In another embodiment the light emitting device has an external power source. In another embodiment the light emitting device has an internal power source. In another embodiment the light emitting device has a DC current power source. In another embodiment the light emitting device has an AC power source. In another embodiment the light emitting device has a battery power source.

In one embodiment the light source of the light emitting device emits a light of any wave length from 400 to 700 nm. In another embodiment the light source of the light emitting device emits a light of a wave length between 400 and 650 nm. In another embodiment the light source of the light emitting device emits a light of a wave length between 400 and 600 nm. In another embodiment the light source of the light emitting device emits a light of a wave length between 400 and 550 nm. In another embodiment the light source of the light emitting device emits a light of a wave length between 400 and 500 nm. In another embodiment the light source of the light emitting device emits a light of a wave length between 425 and 475 nm. In another embodiment the light source of the light emitting device emits a light of a wave length between 430 and 470 nm. In another embodiment the light source of the light emitting device emits a light of a wave length between 440 and 465 nm. In another embodiment the light source of the light emitting device emits a light of a wave length between 450 and 460 nm. In another embodiment the light source of the light emitting device emits a light of a wave length of 450 nm. In another embodiment the light source of the light emitting device emits a light of a wave length of 460 nm.

In one embodiment the light source of the light emitting device emits a light pulse at a rate between 600 pulses/minute to 2 pulses/hour. In another embodiment the light source of the light emitting device emits a light pulse at a rate between 300 pulses/minutes to 4 pulses/hour. In another embodiment the light source of the light emitting device emits a light pulse at a rate between 120 pulses/minutes to 12 pulses/hour. In another embodiment the light source of the light emitting device emits a light pulse at a rate between 60 pulses/minute to 60 pulses/hour. In another embodiment the light source of the light emitting device emits a light pulse at a rate between 30 pulses/minute to 2 pulses/minute. In another embodiment the light source of the light emitting device emits a light pulse at a rate between 20 pulses/minute to 3 pulses/minute. In another embodiment the light source of the light emitting device emits a light pulse at a rate between 10 pulses/minute to 4 pulses/minute. In another embodiment the light source of the light emitting device emits a light pulse at a rate between 8 pulses/minute to 5 pulses/minute.

In one embodiment the light source of the light emitting device emits a light of any intensity from 0 and 4,000 lux. In one embodiment the light source of the light emitting device emits a light of an intensity between 0 and 4,000 lux. In one embodiment the light source of the light emitting device emits a light of an intensity between 1 and 4,000 lux. In another embodiment the light source of the light emitting device emits a light of an intensity between 50 and 3,000 lux. In another embodiment the light source of the light emitting device emits a light of an intensity between 100 and 2,000 lux. In another embodiment the light source of the light emitting device emits a light of an intensity between 150 and 1,000 lux. In another embodiment the light source of the light emitting device emits a light of an intensity between 150 and 500 lux. In another embodiment the light source of the light emitting device emits a light of an intensity between 150 and 450 lux. In another embodiment the light source of the light emitting device emits a light of an intensity between 150 and 400 lux. In another embodiment the light source of the light emitting device emits a light of an intensity between 150 and 250 lux. In another embodiment the light source of the light emitting device emits a light of an intensity 150 lux.

In one embodiment the device is a smart device. In one embodiment the smart device is a smart phone. In one embodiment the smart device is a tablet. In one embodiment the smart device is a personal assistant device. In one embodiment the smart device is a laptop computer. In one embodiment the smart device is an ultrabook computer. In one embodiment the smart device is a notebook computer.

In one embodiment the smart phone is an iphone. In one embodiment the tablet is an ipad.

In one embodiment the smart device awakens an animal. In another embodiment the smart device awakens a mammal. In another embodiment the smart device awakens a pet. In another embodiment the smart device awakens dog or cat. In another embodiment the smart device awakens domestic animals. In another embodiment the smart device awakens a commercial production of animal. In another embodiment the smart device awakens a pig, cow, or chicken. In another embodiment smart device awakens a primate. In another embodiment smart device awakens a human.

In one embodiment the smart device stimulates hormone production in an animal. In another embodiment the smart device stimulates hormone production in a mammal. In another embodiment the smart device stimulates hormone production in a pet. In another embodiment the smart device stimulates hormone production in dog or cat. In another embodiment the smart device stimulates hormone production in domestic animals. In another embodiment the smart device stimulates hormone production in a commercial production of animal. In another embodiment the smart device stimulates hormone production in a pig, cow, or chicken. In another embodiment smart device stimulates hormone production in a primate. In another embodiment smart device stimulates hormone production in a human.

In one embodiment the smart device inhibits hormone production in an animal. In another embodiment the smart device inhibits hormone production in a mammal. In another embodiment the smart device inhibits hormone production in a pet. In another embodiment the smart device inhibits hormone production in dog or cat. In another embodiment the smart device inhibits hormone production in domestic animals. In another embodiment the smart device inhibits hormone production in a commercial production of animal. In another embodiment the smart device inhibits hormone production in a pig, cow, or chicken. In another embodiment smart device inhibits hormone production in a primate. In another embodiment smart device inhibits hormone production in a human.

In one embodiment the smart device has a power source. In another embodiment the smart device has an external power source. In another embodiment the smart device has an internal power source. In another embodiment the smart device has a DC current power source. In another embodiment the smart device has an AC power source. In another embodiment the smart device has a battery power source.

In one embodiment the light source of the smart device emits a light of any wave length from 400 to 700 nm. In another embodiment the light source of the smart device emits a light of a wave length between 400 and 650 nm. In another embodiment the light source of the smart device emits a light of a wave length between 400 and 600 nm. In another embodiment the light source of the smart device emits a light of a wave length between 400 and 550 nm. In another embodiment the light source of the smart device emits a light of a wave length between 400 and 500 nm. In another embodiment the light source of the smart device emits a light of a wave length between 425 and 475 nm. In another embodiment the light source of the smart device emits a light of a wave length between 430 and 470 nm. In another embodiment the light source of the smart device emits a light of a wave length between 440 and 465 nm. In another embodiment the light source of the smart device emits a light of a wave length between 450 and 460 nm. In another embodiment the light source of the smart device emits a light of a wave length of 450 nm. In another embodiment the light source of the smart device emits a light of a wave length of 460 nm.

In one embodiment the light source of the smart device emits a light pulse at a rate between 600 pulses/minute to 2 pulses/hour. In another embodiment the light source of the smart device emits a light pulse at a rate between 300 pulses/minutes to 4 pulses/hour. In another embodiment the light source of the smart device emits a light pulse at a rate between 120 pulses/minutes to 12 pulses/hour. In another embodiment the light source of the smart device emits a light pulse at a rate between 60 pulses/minute to 60 pulses/hour. In another embodiment the light source of the smart device emits a light pulse at a rate between 30 pulses/minute to 2 pulses/minute. In another embodiment the light source of the smart device emits a light pulse at a rate between 20 pulses/minute to 3 pulses/minute. In another embodiment the light source of the smart device emits a light pulse at a rate between 10 pulses/minute to 4 pulses/minute. In another embodiment the light source of the smart device emits a light pulse at a rate between 8 pulses/minute to 5 pulses/minute.

In one embodiment the light source of the smart device emits a light of any intensity from 0 and 4,000 lux. In one embodiment the light source of the smart device emits a light of an intensity between 0 and 4,000 lux. In one embodiment the light source of the smart device emits a light of any intensity from 1 and 4,000 lux. In one embodiment the light source of the smart device emits a light of an intensity between 1 and 4,000 lux. In another embodiment the light source of the smart device emits a light of an intensity between 50 and 3,000 lux. In another embodiment the light source of the smart device emits a light of an intensity between 100 and 2,000 lux. In another embodiment the light source of the smart device emits a light of an intensity between 150 and 1,000 lux. In another embodiment the light source of the smart device emits a light of an intensity between 150 and 500 lux. In another embodiment the light source of the smart device emits a light of an intensity between 150 and 450 lux. In another embodiment the light source of the smart device emits a light of an intensity between 150 and 400 lux. In another embodiment the light source of the smart device emits a light of an intensity between 150 and 250 lux. In another embodiment the light source of the smart device emits a light of an intensity 150 lux.

In one embodiment the smart device controls a larger circuit to operate lights in a structure where people sleep or live (e.g., dormitory, barracks, fire station, etc.) to either wake up or respond to a call or emergency.

In one embodiment the smart device controls a time keeper to silently alert a person when time is up or the changing of the hour.

Other Embodiments

It is to be understood that while the invention has been described in conjunction with the detailed description thereof, the foregoing description is intended to illustrate and not limit the scope of the invention, which is defined by the scope of the appended claims. For example, although the above description relates to humans, various aspects of the invention might also be applied to other animals (e.g., chicken, mice, rats, cows, sheep, monkeys, apes, horses, goats, cats, dogs, pigs, etc.) by making appropriate modifications to the described methods. Other aspects, advantages, and modifications are within the scope of the following claims.

The invention claimed is:

1. A method of awakening an animal, comprising: a) programming a controller of a smart device to emit light at a selected time, wave length, pulse rate and intensity, b) emitting the light from the smart device at the selected time, c) emitting the light from the smart device at the selected wave length from 400 nm to 700 nm, d) emitting the light from the smart device at the selected pulse rate from 600 pulses/minute to 2 pulses/hour, e) emitting the light from the smart device at the selected intensity from 0 lux to 4,000 lux, f) exposing the animal to the light from the smart device, and g) awakening the animal.

2. The method of claim 1, wherein the controller is activated by an external electronic signal.

3. The method of claim 1, wherein the wave length is any wave length from 400 nm to 650 nm.

4. The method of claim 3, wherein the wave length is any wave length from 400 nm to 500 nm.

5. The method of claim 1, wherein the pulse rate is any pulse rate from 300 pulses/minute to 4 pulses/hour.

6. The method of claim 5, wherein the pulse rate is any pulse rate from 120 pulses/minute to 12 pulses/hour.

7. The method of claim 1, wherein the intensity is any intensity from 50 lux to 3,000 lux.

8. The method of claim 7, wherein the intensity is any intensity from 100 lux to 2,000 lux.

9. The method of claim 1, wherein the smart device is selected from the group consisting of a smart phone, a tablet, a personal assistant device, a laptop computer, a ultrabook computer and a notebook computer.

10. The method of claim 9, wherein the smart device is a smart phone.

11. The method of claim 10, wherein the smart phone is an iphone.

12. The method of claim 9, wherein the smart device is a tablet.

13. The method of claim 12, wherein the smart device is an ipad.

14. The method of claim 1, wherein the smart device emits light pulses at a pre-determined pulse rate.

15. The method of claim 1, wherein the smart device emits light at a pre-determined wave length range.

16. The method of claim 1, wherein the smart device emits light with a pre-determined intensity.

17. The method of claim 1, wherein the smart device emits a light with an intensity that is gradually increased from zero to maximum value.

18. An application on a smart device that programs the smart device to use the method of claim 1.

* * * * *